United States Patent [19]
Bednarski et al.

[11] Patent Number: 4,745,109
[45] Date of Patent: May 17, 1988

[54] SUICIDE INHIBITORS OF AROMATASE

[75] Inventors: Patrick J. Bednarski; David J. Porubek; Sidney D. Nelson, all of Seattle, Wash.

[73] Assignee: Washington Research Foundation, Seattle, Wash.

[21] Appl. No.: 642,620

[22] Filed: Aug. 20, 1984

[51] Int. Cl.$^4$ .......................... A61K 31/56; C07J 1/00
[52] U.S. Cl. ................... 514/170; 260/397.3; 260/397.4; 514/177
[58] Field of Search ............... 514/170, 176, 177; 260/397.3, 397.4

[56] References Cited

U.S. PATENT DOCUMENTS 4,473,564 9/1984 DeWinter et al. .................. 514/170

FOREIGN PATENT DOCUMENTS 0100566 2/1984 European Pat. Off. .

OTHER PUBLICATIONS

Chemical Abstracts; vol. 80 (1974), #15120q; Schade et al.
Chemical Abstracts; vol. 83 (1975), #43577z; Ponsold et al.
Chemical Abstracts; vol. 102 (1985), #200130d; Bednarski et al.
Chemical Abstracts; vol. 104 (1986), #51017j; Loozen et al.
Abul-Hajj, Y. J., *J. Steroid Biochem.*, 13, 1395 (1980).
Brodie, A. M. H., *Cancer Res.*, 42 3312s (1982).
Brodie, A. M. H.; Brodie, H. J.; Garrett, W. H.; Hendrickson, J. R.; Marsh, D. A.; and Tsai-Morris, Chon-Hwa, *Biochem. Pharm.*, 31, 2017 (1982).
Powles, T. J., Seminars in Oncology, 10, suppl. 4, 20 (1983).
Brodie, A. M. H., *J. Endocrinol. Invest.*, 2, 445 (1979).
Fishman, J., *Cancer Res.*, 42, 3277s (1982).
Marcotte, P. A., and Robinson, C. H., Biochemistry, 21, 2773 (1982).
Flynn, G. A.; Johnston, J. O.; Wright, C. L.; and Metcalf, B. W.; *Biochem Biophys. Res. Comm.*, 103, 913 (1981).
Metclaf, B. W.; Wright, C. L.; Burhart, J. P.; and Johnston, J. O., *J. Am. Chem Soc.*, 103, 3221 (1981).
Menard, R. H.; Guenther, T. M.; Taburet, A. M.; Kon, H.; Pohl, L. R.; Gillette, J. R.; Gelboin, H. V.; and Trager, W. F., *Mol. Pharm.*, 16, 997 (1979).
Baba, S.; Shinohara, Y.; and Kasuya, Y., *J. Labelled Compounds and Radiopharm.*, 14, 783 (1978).
Ponsold, Von K.; Schade, W.; and Wunderwold, W., *J. f. prakt. Chemie.*, 317, 307, 319 (1975).
Beard, C. D.; Baum, K.; and Grakanskas, V., *J. Org. Chem*, 38,3673 (1973).
Beretta, E.; Cinquini, M.; Colonna, S.; and Formasier, R., *Synthesis*, 425 (1974).

(List continued on next page.)

*Primary Examiner*—Leonard Schenkman
*Assistant Examiner*—Joseph A. Lipovsky
*Attorney, Agent, or Firm*—Seed and Berry

[57] ABSTRACT

Thiol-substituted synthetic steriod hormones or androgens having a testosterone ring system backbone are used to inhibit aromatase's catalyzed conversion of $C_{19}$ androgens having a $\Delta^4$,3-ketone group to estrogens in the treatment of estrogen-dependent tumors, such as metastatic breast cancer in postmenopausal females.

The compounds have the general formula:

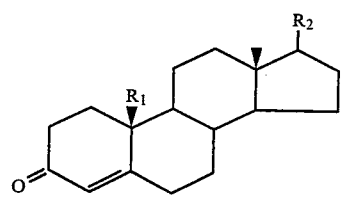

wherein $R_1$ = a thiol, such as —SH or —CH$_2$SH, and $R_2$ =◄OH or=O. The preferred synthetic hormones are 17β-hydroxy-10β-mercaptoestr-4-en-3-one, 19-mercaptoandrost-4-en-3,17-dione, and 10β-mercaptoandrost-4-en-3,17-dione.

18 Claims, 4 Drawing Sheets

OTHER PUBLICATIONS

Couey, D. F.; Hood, W. F.; and Parikh, V. D., *J. Biol Chem.*, 256, 1076 (1981).

Thompson, E. A., and Siiteri, P. K., *J. Biol. Chem.*, 249, 5364 (1974).

Dixon, M., and Webb, E. C., "Enzymes," 3rd ed., Longman Group Ltd., London, 1979; pp. 369–381.

Rando, R. R., in "Methods in Enzymology XLVI," Jakoby, W. B., and Wilchik, M., eds., Academic Press, NY 1977.

Mannervik, B., "Metabolic Basis of Detoxification: Metabolism of Functional Groups," Jakoby, W. B.; Bend, J. R.; and Caldwell, J., eds., Academic Press, NY., 1982, pp. 192–193.

Lowry, O. H.; Rosebraugh, N. J.; Farr, A. L.; and Randall, R. J., *J. Biol. Chem.*, 193, 265 (1951).

Troner, M. B., *Cancer Res.*, 42, 3402s–3404s (1982).

Powles, T. J. et al, *The Lancet*, Jun. 23, 1894, 1369–1372.

SUICIDE INHIBITORS OF AROMATASE

This research was supported by Grant GM25418 from the National Institutes of Health.

DESCRIPTION

TECHNICAL FIELD

The present invention relates to suicide inhibitors of aromatase which block the conversion of $C_{19}$ androgens having a $\Delta^4$,3-ketone group to $C_{18}$ estrogens. The inhibitors are particularly useful for treating estrogen-dependent carcinomas since they irreversibly block the formation of estrogen by aromatase.

BACKGROUND ART

The observation that approximately 35% of breast cancers are estrogen dependent has stimulated research into methods of limiting estrogen production. Initial efforts were to surgically remove the primary source of estrogen (ovaries) or the primary sources of their biosynthetic steroid precursors, the androgens (adrenal glands). While these methods are often successful, work has been directed in recent years towards a more effective inhibition of estrogen production in a nonintrusive, less traumatic way. (Abul-Hajj, Y. J., *J. Steroid Biochem.*, 13 1395 (1980); Brodie, A. M. H., *Cancer Res.*, 42, 3312s (1982); Brodie, A. M. H.; Brodie, H. J.; Garrett, W. H.; Hendrickson, J. R.; Marsh, D. A.; and Tsai-Morris, Chon-Hwa, *Biochem. Pharm.*, 31, 2017 (1982); and Powles, T. J., *Seminars in Oncology*, 10, suppl. 4, 20 (1983).) Inhibition of the last enzymatic step, the aromatization of the $A^4$,3-keto androgens to the phenolic estrogens, would seem the most effective and least disruptive based upon knowledge of the enzymes involved in the biosynthesis of estrogens from cholesterol. The enzyme responsible for this conversion is a unique cytochrome P-450 monooxygenase complex known as "aromatase" (Brodie, A. M. H., *J. Endocrinol. Invest.*, 2, 445 (1979)) that requires $O_2$ and NADPH to catalyze three sequential hydroxylations of the androgen precursor followed by a spontaneous chemical aromatization of the A ring to yield the phenolic estrogens. A proposed mechanism for aromatase activity is shown in FIG. 1.

Based upon this mechanism, others (Marcotte, P. A., and Robinson, C. H., *Biochemistry*, 21, 2773 (1982); Flynn, G. A.; Johnston, J. O.; Wright, C. L.; and Metcalf, B. W., *Biochem. Biophys. Res. Comm.*, 103, 913 (1981); and Metcalf, B. W.; Wright, C. L.; Burhart, J. P.; and Johnston, J. O., *J. Am. Chem. Soc.*, 103, 3221 (1981)) have proposed suicide inhibitors for aromatase. Troner (*Cancer Res.*, 42, 3402s–3404s (1982)) and Powles et al. (*The Lancet*, June 23, 1984, 1369–1372) suggest aminoglutethimide (AG), a competitive inhibitor, with other compounds to treat metastatic breast cancers. AG, however, is a sedative which has the side effect of lethargy. Also, AG is not specific to aromatase, so it disrupts enzymatic pathways other than the androgen-estrogen pathway.

Menard et al. (*Mol. Pharm.*, 16, 997 (1979)) discloses thiol steroids as suicide inhibitors of P-450 steroid hydroxylase activity.

Hormonal treatment of tumors and steroid research are active fields with great promise. The appropriate inhibitors should be specific to the enzyme pathway where inhibition is sought. Thus, the synthetic hormones of the present invention offer promise, as will be explained.

DISCLOSURE OF INVENTION

A suicide inhibitor of aromatase is useful for treating estrogen-dependent breast cancers, particularly for postmenopausal metastatic carcinomas. The inhibitors block the conversion of $C_{19}$ androgens having a $\Delta^4$,3-ketone group to $C_{18}$ estrogens and include thiol-substituted androgens having a testosterone ring system backbone with the thiol substituent at the 10 carbon. Generally, the thiol substituent is —SH or —CH$_2$SH, but any thiol may be used which is short enough to avoid stearic hindrance. The synthetic hormones, 17β-hydroxy-10β-mercaptoestr-4-en-3-one(I), 19-mercaptoandrost-4-en-3,17-dione(II), and 10β-mercaptoandrost-4-en-3,17-dione(III) are highly preferred.

The structural formulae are:

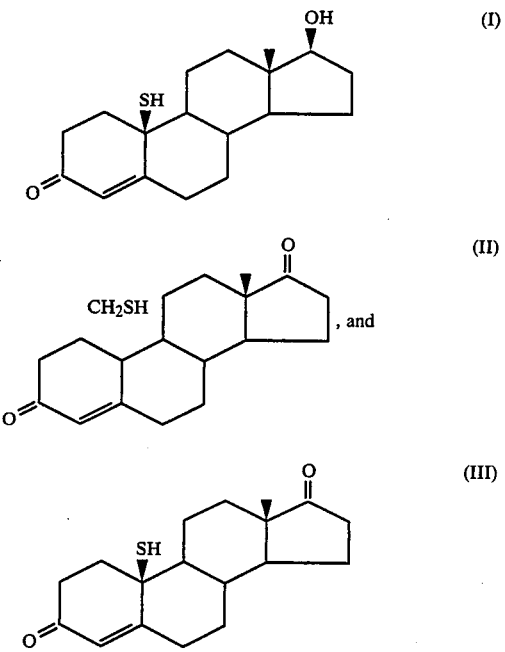

The thiol (—SH) or methylenethiol (—CH$_2$SH) at the 10 position of the androgen apparently covalently bonds within the active site of aromatase to irreversibly inhibit the hydroxylase activity of aromatase.

A method for inhibiting aromatase, a method for treating estrogen-dependent cancers, and novel thiol-substituted synthetic steroid hormones are described and claimed.

BEST MODE FOR CARRYING OUT THE INVENTION

For purposes of this description, a "testosterone ring system backbone" shall mean a carbon chain of the following formula:

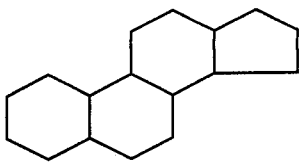

This backbone does not represent the degree of saturation or substitution, but rather shows the general carbon configuration. Detailed structural formulas, such as that for the 19-mercaptoandrost-4-en-3,17-dione,

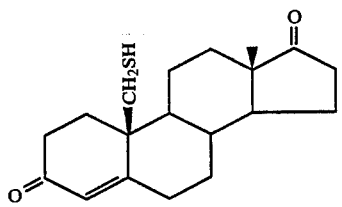

indicate the saturation, substituents, and stereochemistry in the conventional manner.

For purposes of this description, the terms "alkylene thiol" and "alkyl mercaptan" shall be synonyms. That is, —CH$_2$SH may be called "methylene thiol" or "methyl mercaptan."

For purposes of this description, the term "synthetic hormone" shall mean a synthesized androgen having a testosterone ring system backbone including substituents which distinguish the androgen from naturally occurring hormones.

The "testosterone ring system" is more commonly called an "estrane ring system" if a β-methyl group is substituted at the 13 carbon. That is, the structure is:

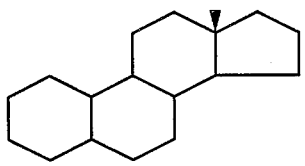

This "estrane ring system" is common to the preferred synthetic hormones of this invention. Please excuse the departure from conventional terminology adapted for this description and claims. The "estrane ring system" is a species of the generic term "testosterone ring system."

1. The Synthesis of 17β-hydroxy-10β-mercaptoestr-4-en-3-one

Figure 1:
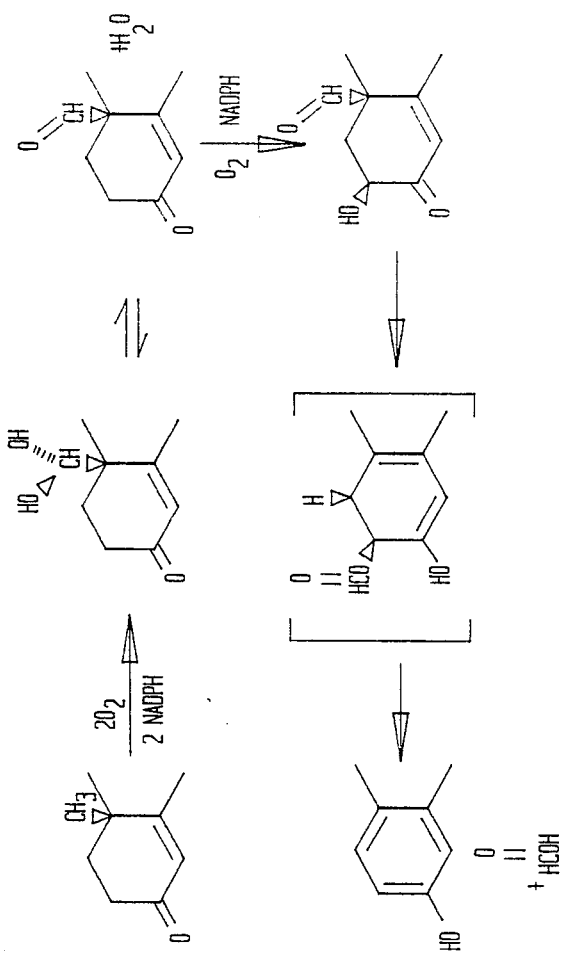
FIG. 1 is a proposed mechanism of the reactions catalyzed by aromatase.
Figure 2:
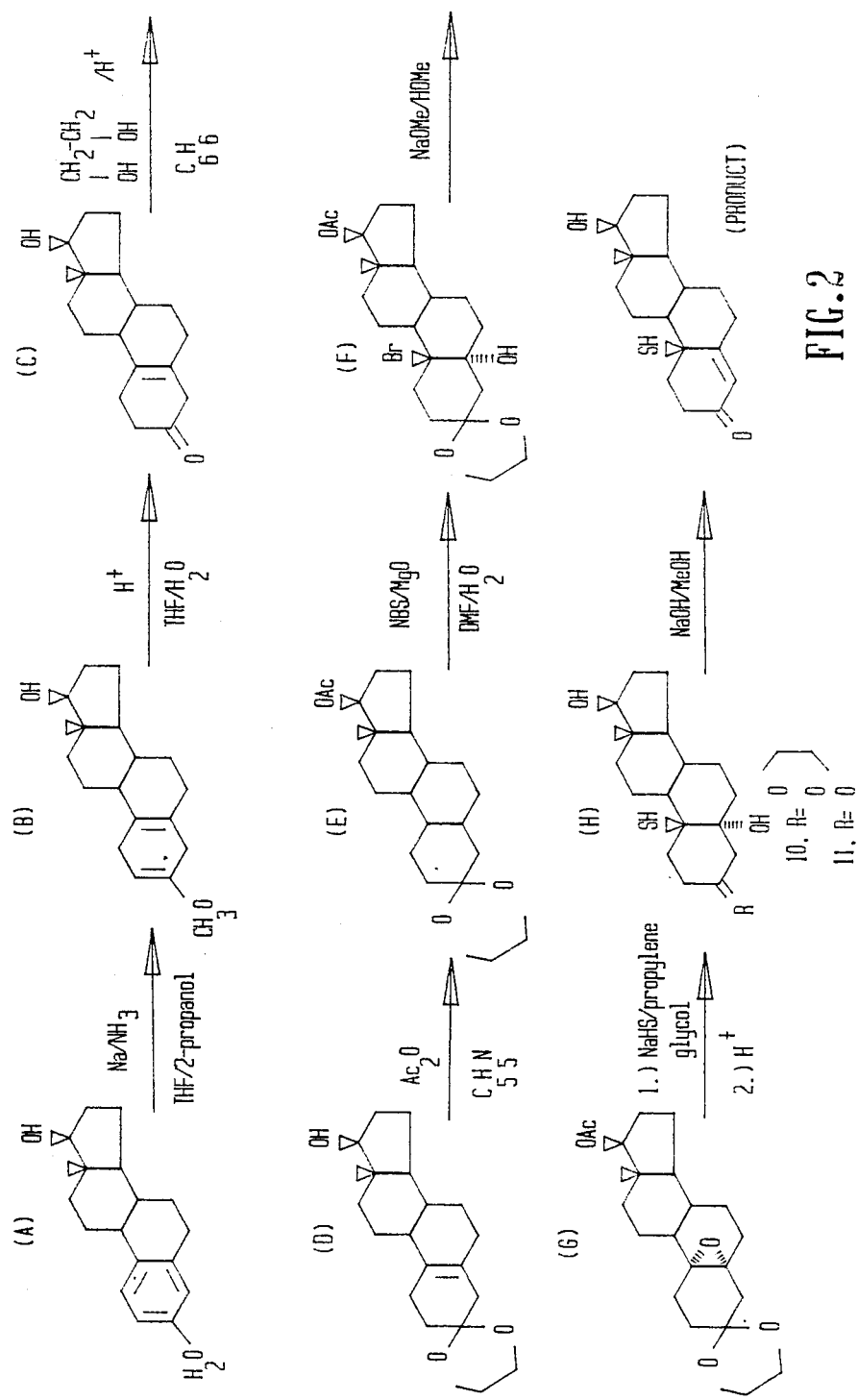
FIG. 2 is a schematic of the synthesis of 17β-hydroxy-10β-mercaptoestr-4-en-3-one.

Modifying the synthesis proposed by Ponsold et al. (*f. prakt. Chemie.*, 317, 307, 319 (1975)), the synthetic hormone is made (as shown in FIG. 2) by reducing estradiol, 3-methyl ether (A) under Birch conditions to an estradiene (B). After protecting the 3-ketone as a ketal (D), and protecting the 17-alcohol as any acetate (E), an acid-catalyzed rearrangement of the diene-produced estra-5(10)-en-17β-ol-3-one (C) provided an intermediate which reacted with N-bromosuccinimide to produce the protected 5β-10αbromohydrin (F). Upon the addition of sufficient base, the 5β-10αbromohydrin (F) was converted to the 5α-10αepoxide (G). A thiol group was added to the 10 carbon by reacting the epoxide with NaHS in ethylene glycol at 140° C. to yield the 5α-hydroxy-10β-mercapto steroid (H). Upon the addition of acid, the 3-ketone is formed. Finally, dehydration under basic conditions provides the desired, thiol-substituted synthetic hormone.

2. Synthesis of 19-mercaptoandrost-4-en-3,17-dione

Figure 3:
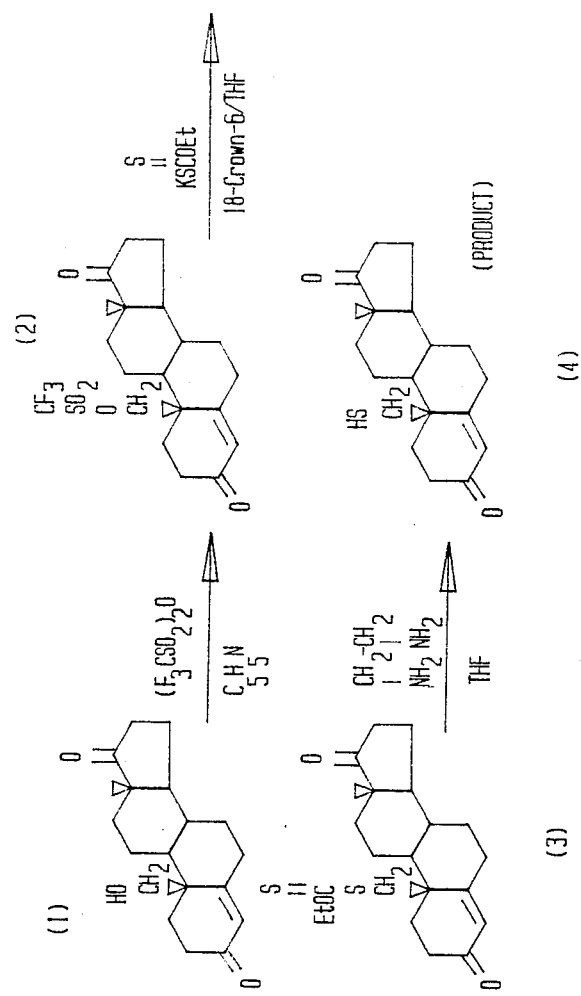
FIG. 3 is a schematic of the synthesis of 19-mercaptoandrost-4-en-3,17-dione.

This synthetic hormone is made (as shown in FIG. 3) by activating the 19-hydroxyl group of 19-hydroxyandrost-4-en-3,17-dione (1) to a 19-triflate (2) using trifluoromethanesulfonic anhydride. The triflyl group could not be successfully displaced with NaHS or KHS in the presence of the crown ether, 18-crown-6, but a xanthogenate functionality (3) was successfully placed on the 19 position with potassium ethylxanthogenate and 18-crown-6. Cleavage of the 19-xanthogenate ester (3) to the 19-thiol was unsuccessful in ethylenediamine, but was accomplished in acceptable yields in ethylenediamine diluted with THF to yield the product (4).

3. Synthesis of 10β-mercaptoandrost-4-en-3,17-dione

Figure 4:
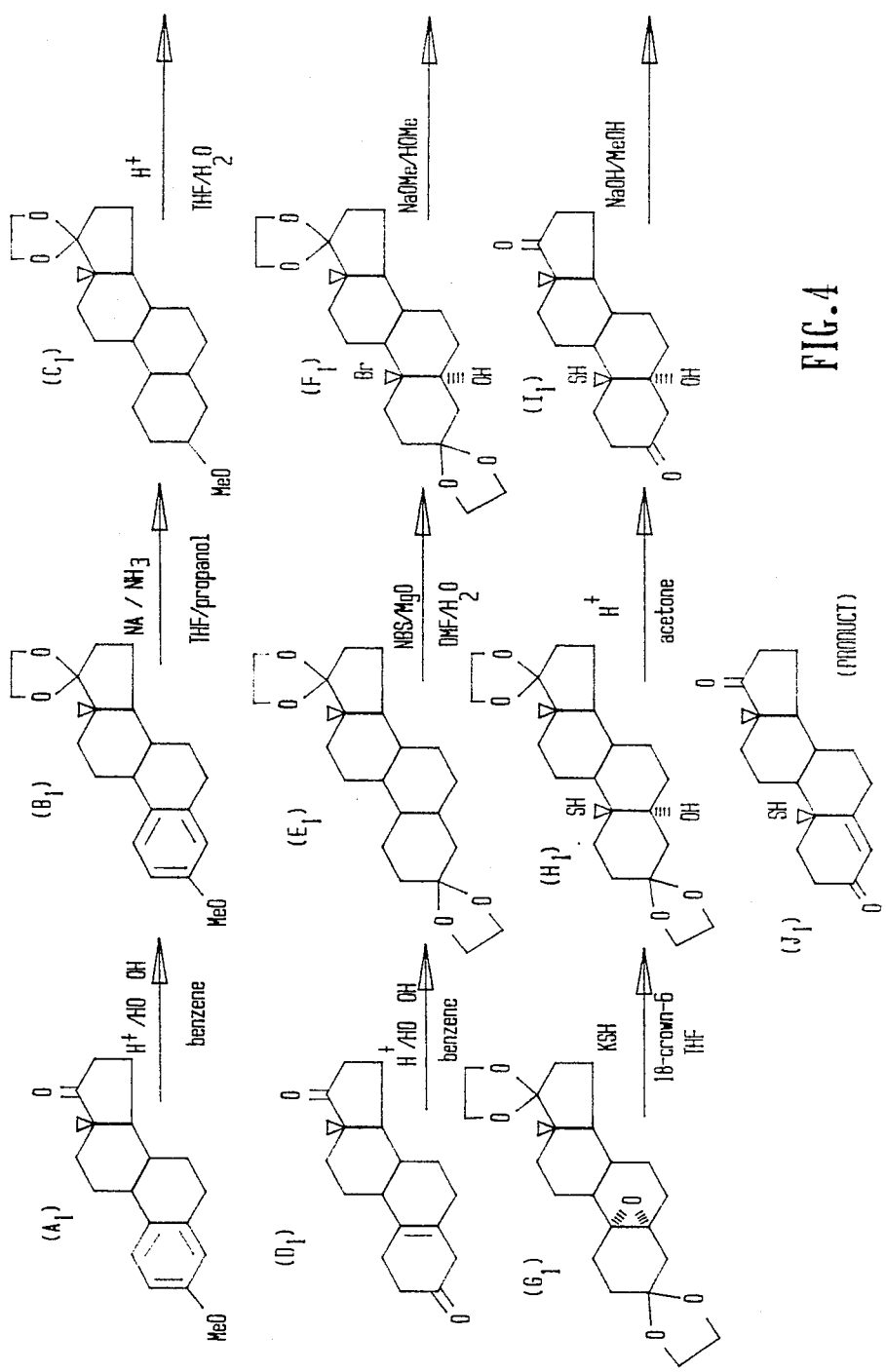
FIG. 4 is a schematic of the synthesis of 10β-mercaptoandrost-4-en-3,17-dione.

Esterdiol, 3-methyl ether (A$_1$) had the 17-ketone protected as a ketal (B$_1$) before reacting under Birch conditions to create the protected estradiene (C$_1$), as shown in FIG. 4. An acid-catalyzed rearrangement of the diene (C$_1$) produced an estra-5(10)-en-3,17-dione (D$_1$) which, in turn, had both ketones protected as ketals (E$_1$) before adding a Bromine to the 19 position. That is, the protected dione (E$_1$) was reacted with N-bromosuccinimide to create a 5β-10α bromohydrin (F$_1$) which was then converted to the 5α,5α epoxide (G$_1$) under basic conditions. A thiol group replaced the epoxide with KHS in 18-crown-6 ether and THF to produce a 5α-hydroxy-10β-mercapto steroid (H$_1$) which was acidified to provide the associated dione (I$_1$) prior to dehydration under basic conditions to yield the desired product (J$_1$).

As can be seen, 19-mercaptoandrost-4-en-3,17-dione and 10β-mercaptoandrost-4-en-3,17-dione differ only in the thiol substituent for the 10 carbon, with the former having a methylene thiol (—CH$_2$SH) while the latter has a sulfhydryl or thiol (—SH). The activity of each compound is expected to be similar, with a faster inhibiting effect provided by the (—SH) compound since its 10 position thiol substituent is shorter. The active site of aromatase apparently is quite sensitive to the length of a substituent on the 10 position. The groups —SH and —CH$_2$SH are highly preferred. Long thiols may be inactive or have a much slower rate of inhibition due to stearic hindrance.

The suicide inhibitors just described are similar structurally to the naturally occurring androgens on which aromatase works to convert C$_{19}$ androgens having a Δ$^4$,3-ketone to C$_{18}$ estrogens. These inhibitors appear to bind covalently to the active site of the aromatase to inhibit the production of estrogen. The binding seems to be irreversible. Because the inhibitors are so similar to the natural androgens on which aromatase operates, the inhibitors are believed to be specific to aromatase and to have no effect on other enzyme systems.

4. Activity of the Synthetic Hormones

The activity of 17β-hydroxy-10β-mercaptoestr-4-en-3-one and 19-mercaptoandrost-4-en-3,17-dione were tested as suicide inhibitors of aromatase according to the method of Coury et al. (*J. Biol. Chem.*, 256, 1076 (1981)) in human placental microsomes. The activity was measured by the well-established tritium release assay according to Thompson et al. (*J. Biol. Chem.*, 249, 5364 (1974)) using 1β,2β-[$^3$H]androstenedione (40–60 Ci/mole) obtained from New England Nuclear in Boston, MA.

Both compounds gave a time-dependent, biphasic loss of enzymatic activity over 70 minutes when NADPH and oxygen were available. Incubation of the inhibitors in the presence of androstenedione showed an increase in the $t_{\frac{1}{2}}$. Incubation with the nucleophile, cysteine, had no effect on the $t_{\frac{1}{2}}$. After 20 hours of diffusion dialysis at 0° C., the activity (inactivity) of the enzyme remained substantially unchanged, indicating that the inhibitors bond covalently to the enzyme.

It is believed that the same results will be obtained with 10β-mercaptoandrost-4-en-3,17-dione and other synthetic hormones of this general type having a thiol substituent at the 10 carbon.

5. Sources of Starting Materials

Estradiol, 3-methyl ether and NADPH are available from Sigman Chemical Co. (St. Louis, MO). 19-Hydroxyandrost-4-en-3,17-dione is available from Aldrich Chemical Co. (Milwaukee, WI). Potassium ethylxanthogenate is available from Pfaltz and Bauer (Stamford, CT). Androstenedione is available from Steraloids (Wilton, NH).

6. Mechanism of Inhibition

Because the thiol synthetic hormone inhibitors of the present invention are quite similar to the natural 3-keto,4-ene androgens on which aromatase works, the thiol probably is activated to an electrophilic moiety by the enzyme and irreversibly binds to nucleophiles within the active site. A freely dissociable enzyme-inhibitor complex may be formed which is converted by the enzyme to a reactive intermediate. This intermediate can react in the pseudo-first-order rate which is observed to produce the irreversible enzyme-inhibitor final complex.

The compounds satisfy the five conditions for a suicide substrate. One, each exhibits a time-dependent, pseudo-first-order rate of enzymate inactivation. Two, the cofactors (NADPH and oxygen) that are required for the normal catalytic processes are also required for the inactivation. Three, reversible substrates, such as androstenedione, protect the enzyme from time-dependent inactivation and slow the rate of inactivation. Four, nucleophiles in the incubate fail to protect the enzyme from inactivation; and, five, the inhibition is irreversible.

The experimental biphasic loss of activity probably results from the metabolic-dependent elimination of the inhibitor from the incubate.

Mixtures of the inhibitors will result in inactivation; only the rate constant will change. The rate constant for 17β-hydroxy-10β-mercaptoestr-4-en-3-one is about three times greater than that for 19-mercaptoandrost-4-en-3,17-dione.

The conversion of androgens to estrogens by aromatase requires six reducing equivalents in the form of NADPH. Activation of the thiol androgen inhibitors would also be expected to require NADPH. Incubations of both inhibitors in the absence of NADPH failed to show time-dependent inactivation of aromatase. At least one equivalent of oxygen would be required for the time-dependent inactivation of aromatase by these inhibitors. Under anaerobic conditions, a complete protection from inactivation by these inhibitors was achieved.

Activation of a suicide substrate to its reactive intermediate apparently occurs at the same enzymatic site responsible for catalysis of the normal substrate. Since the suicide substrates are competing for this same site as the normal substrates of aromatase (i.e., androstenedione), the presence of androstenedione slows the rate of loss of enzymatic activity due to these two inhibitors. Suicide inhibition requires that once the suicide substrate is activated, it immediately binds in a covalent fashion at the active site without first diffusing into the incubation media. If the activated intermediate diffuses out of the active site before it inactivates the enzyme, nucleophiles present in the incubation could react with the electrophilic intermediate and slow the time-dependent loss of activity. For the suicide substrates, the presence of the nucleophile, cysteine, in the incubation did not protect aromatase from time-dependent loss of activity, which indicates that whatever species is formed probably reacts at the enzyme active site before reversible diffusion out of the site. Finally, attempts to reactivate the suicide substrate-inactivated enzyme complex using diffusion dialysis were unsuccessful, indicating the covalent nature of the substrate-enzyme complex.

Although the mechanism of inhibition is not completely understood, the requirement that both NADPH and oxygen be present for inhibition indicates that an oxidized species is the reactive intermediate. Oxidation of thiol groups in positions of the androgen nucleus that are normally hydroxylated by aromatase might be expected to form sulfenic acids. These potent electrophiles could bind in a covalent manner with nucleophiles in the enzymatic active site and irreversibly inhibit the enzyme.

For treating estrogen-dependent cancers, such as metastatic breast cancers in postmenopausal patients, the synthetic hormones probably will be ingested or injected in a prodrug form wherein the thiol substituent is protected by an acetate

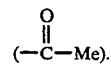

Factors in the blood will quickly convert this protected prodrug to the active thiol form to allow inhibition of aromatase. Administering an effective amount of the inhibitors or prodrugs should result in a blocking of the estrogen production pathway at the final step by blocking the conversion of the $C_{19}$ androgens to $C_{18}$ estrogens. Only aromatase should be inhibited. Serious side effects, such as lethargy or tumor lysis syndrome, as noted for aminoglutethimide complexes, should be absent. Further testing continues.

7. Details of the Syntheses a. 17β-hydroxy-estr-5(10)en-3-one 80 ml of freshly distilled ammonia stirred in a dry-ice-/acetone bath, 17β-estradiol,3-methyl ether (4.97 g, 17.2 mmol), and 60 ml 1:1 THF/2-propanol were mixed. To this mixture, sodium metal (~4.3 g, 190 mmol) in small portions was added over 15 minutes. The reaction was stirred for three hours, after which time all the sodium metal had been consumed. Methanol (20 ml) was added and the ammonia was allowed to evaporate overnight at room temperature. THF was removed under reduced pressure and 100 ml water was added. The resulting precipitate was collected by suction filtration and washed generously with water. The white solid was dried under reduced pressure. $^1$H NMR (CCl$_4$ δ2.55 (m, 4H), 3.45 (s, 3H) 4.45 (m, 1H), 4.70 (m, 1H).

The crude estra-5(10)dien-3,17β-ol,3-methyl ether was dissolved in 25 ml THF and 12 ml H$_2$O. 1.5 ml of 96% H$_2$SO$_4$ was added dropwise. After 45 minutes, enough (NH$_4$)$_2$SO$_4$ was added to saturate the aqueous phase, and the organic phase was extracted with CH$_2$Cl$_2$. The organic phase was washed with water, and then washed with a saturated solution of NaHCO$_3$/NH$_4$SO$_4$, dried over MgSO$_4$, filtered, and concentrated on a rotary evaporator to give 4.28 g of a light yellow solid. Recrystallization (ethyl acetate/hexane) gave 2.73 g of a white crystalline solid; mp 175°-180° C. (Lit. 181°-182° C.), $^1$H NMR: (CDCl$_3$) δ2.40 (broad s, 4H), 2.70 (broad s, 2H), 3.70 (m, 1H).

b. 17β-acetoxy-estr-5-(10)-en-3-cycloethyleneketal

To 150 ml dry benzene and 16 ml ethylene glycol, estra-5(10)-en-17β-ol-3-one (2.80 g, 10.2 mmol) and p-toluenesulfonic acid (0.16 g, 0.98 mmol) were added. The reaction mixture was refluxed for 19 hours with continuous removal of the water that was produced by means of a Dean-Stark trap. After cooling, the benzene fraction was washed with 5% NaHCO$_3$, twice with water, dried over MgSO$_4$, and concentrated under reduced pressure to give 3.31 g of a white solid; $^1$H NMR (CDCl$_3$) δ3.70 (m, 1H), 3.95 (d, 4H); IR (Nujol) 3420 (broad), 1670 cm$^{-1}$.

The crude 3,3-ethylenedioxy-17β-hydroxyestran-5(10)ene (3.31 g, 10.4 mmol) was dissolved in 10 ml dry pyridine and acetic anhydride (5.0 ml, 50 mmol) and allowed to stand four hours at room temperature. To this mixture, 50 ml CHCl$_3$ and 30 ml water were added. The organic phase was separated and washed twice with water, twice with ice-cold 3% H$_2$SO$_4$, once with 5% NaHCO$_3$, and finally, once again with water. The organic phase was dried over MgSO$_4$, filtered, and concentrated under reduced pressure to give 3.48 g of a white solid. TLC (CH$_2$Cl$_2$) R$_f$0.67; $^1$H NMR (CDCl$_3$) δ2.05 (s), 3.95 (d, 4H), 4.68 (to broad t, 1H); IR (Nujol) 1735, 1670, 1240, 1105, 1085, 1055, 1040 and 945 cm$^{-1}$.

c. 17β-acetoxy-estr-5(10)epoxy-3-cycloethylenketal

To a stirred solution of crude 17β-acetoxy-3,3-ethylenedioxy-estran-5(10)-ene (3.48 g, 9.7 mmol) in 45 ml DMF and 12 ml water, N-bromosuccinimide (3.45 g, 19.4 mmol) and MgO (0.39 g, 9.7 mmol) were added. After stirring for two hours, 100 ml water was added and the resulting precipitate was collected by suction filtration. The precipitate was washed with water and dissolved in CH$_2$Cl$_2$, and the organic phase washed three times with water, dried over MgSO$_4$, filtered, and concentrated under reduced pressure to give 3.59 g of a white crystalline solid; TLC (CH$_2$Cl$_2$) R$_f$ 01.56. The crude solid (3.59 g, 7.86 mmol) was stirred in 50 ml MeOH under N$_2$ at 6° C., and 7 ml of a 21% NaOMe/MeOH solution was added dropwise. The reaction was stirred for eight hours at 6° C. Following the addition of 120 ml of ice-cold water, the reaction mixture was extracted four times with CH$_2$Cl$_2$. The organic phases were combined and washed with water, dried over MgSO$_4$, and concentrated under reduced pressure to yield 2.88 g of a yellow oil. Column chromatography on Florisil ® using 5% ethyl acetate/CHCl$_3$ as eluant yielded 1.34 g of a white solid; TLC (5% ethyl acetate/CH$_2$Cl$_2$) R$_f$0.80; $^1$H NMR (CDCl$_3$) δ2.05 (s), 3.90 (s, 4H), 4.65 (m, 1H); MS, m/e 376 (42, M+), 359 (33), 317 (16), 316 (31), 274 (22), 256 (33), and 99 (100).

d. 5α,17β-dihydroxy-10B-mercapto-estra-3-cycloethyleneketal

Sodium hydrogen sulfide (2.59 g, 46.2 mmol) was added to a stirred suspension of 17β-acetoxy-5α,10α-epoxy-3-estrane-ethylenedioxy (1.74 g, 4.62 mmol) in 50 ml ethylene glycol, and the reaction was placed under a nitrogen atmosphere. The reaction was warmed to 140° C. for two hours, cooled, and poured into 200 ml of a 5% Na$_2$SO$_4$ solution. This mixture was shaken for times with CHCl$_3$, and the organic phases were combined and washed two times with water, dried over MgSO$_4$, filtered, and concentrated under reduced pressure to give 1.49 g of a light tan solid. Column chromatography on Florisil ® using 50% ethyl ether/cyclohexane as eluant gave 0.60 g of solid. A recrystallized sample from cyclohexane gave a white amorphous solid, mp 180°-184° C. (Lit. 183°-186° C., acetone); $^1$H NMR (CDCl$_3$) δ3.70 (m, 1H), 3.95 (s, 4H), 4.45 (s, exch.); MS m/e 368 (5, M+), 350 (80), 335 (16), 317 (100), 316 (27), 99 (46); IR (Nujol) 3400 (broad), 1115, 1070, 1010, 830 cm$^{-1}$.

e. 5α,17β-dihydroxy-10β-mercapto-estr-3-one 3,3-ethylenedioxy-10β-mercapto-estra-5α,17β-diol (0.60 g, 1.6 mmol) and p-toluenesulfonic acid (0.20 g, 1.0 mmol) were dissolved in 100 ml acetone and stirred overnight under a nitrogen atmosphere. After adding 75 ml of a 5% NaHCO$_3$ solution, the acetone was removed on a rotary evaporator and 75 ml water was added. The aqueous phase was extracted four times with CHCl$_3$, and the organic phases were combined and washed with water, dried over MgSO$_4$, filtered, and concentrated under reduced pressure to give 0.65 g of a tan solid. Column chromatography on Florisil ® using 50:50 ethyl ether/chloroform as eluant gave 0.40 g of product. A recrystallized sample from benzene gave clear crystals, mp 194°-200° C. (Lit. 195°-205° C.); positive Ellman's test for thiols; $^1$H NMR (CDCl$_3$) δ3.70 (m).

f. 17β-hydroxy-10β-mercapto-estr-4-en-one

5α,17β-dihydroxy-10β-mercapto-estran-3-one (the product of e.) (0.38 g, 1.2 mmol) in 25 ml of a 0.1M NaOH/MeOH solution was refluxed under argon for one hour. After cooling in ice, 5.0 ml of a 1.0M HCl solution was added, and the reaction mixture was concentrated on the rotary evaporator. 50 ml water was added and the mixture was extracted three times with CHCl$_3$. The organic phases were combined, washed with 5% NaHCO$_3$ and water, dried over MgSO$_4$, filtered, and concentrated under reduced pressure to give 0.36 g of an organic solid. Column chromatography on Silica Gel 60 (0.063–0.200 mm) with 50% ethyl ether/chloroform yielded 0.18 g of product, which was recrystallized from acetone to give 126 mg of clear crystals; mp 175°–178° C., (Lit. mp 178°–182° C.); $[\alpha]_D$ ($\alpha$=0.5 g/100 ml, chloroform)= +279°, (Lit. $[\alpha]_D$= +268°); UV (acetonitrile) max=238 nm (Lit. $\lambda$max=241 nm); IR (Nujol) 3380 (br), 2500, 1650, 1605, 1350, 1315, 1275, 1220, 1155, 1130, 1050, 1020, 885, 820, and 765 cm$^{-1}$; $^1$H NMR (CDCl$_3$) $\delta$3.65 (t, 1H), 5.65 (s, 1H), MS m/z 306 (M+, 13) 273 (100), 272 (62), 255 (20), 213 (40); Anal. C$_{18}$H$_{20}$O$_2$S C,H,O,S.

g. 19-ethylxanthogenyl-androst-4-en-3,17-dione 19-hydroxy-4-androstene-3,17-dione (0.58 g, 1.92 mmol) in 8 ml cold pyridine was added dropwise to a stirred solution of trifluoromethanesulfonic anhydride (0.60 ml, 1.0 g, 3.57 mmol) in 5 ml cold pyridine under nitrogen. The reaction was allowed to warm to room temperature; and after one hour, 100 ml cold CH$_2$Cl$_2$ was added. The reaction mixture was washed three times with a cold 1M H$_2$SO$_4$ solution, then washed with cold 5% NaHCO$_3$ and cold water, was dried over MgSO$_4$, filtered, and concentrated on the rotary evaporator to give 0.71 g of product as a light-orange solid; IR (Nujol) 1735, 1160, 1615, 1405, 140, 1215, 1195, 1140, 935 and 825 cm$^{-1}$; NMR (CDCl$_3$) $\delta$4.84 (d of d, 2H), 6.10 (s, 1H); MS m/z 434 (M+, 79), 283 (100).

A mixture of crude 19-trifly-androstene-3,17-dione (0.71 g, 1.6 mmol), potassium ethylxanthogenate (0.51 g, 3.2 mmol), and 18-crown-6 (42 mg, 0.16 mmol) in 20 ml dry THF was stirred at room temperature for 20 hours under nitrogen. To the reaction mixture, 100 ml CH$_2$Cl$_2$ was added and the resulting mixture was washed three times with a saturated solution of KCl and twice with water, was dried over MgSO$_4$, filtered, and concentrated on the rotary evaporator to give 0.71 g of an orange solid. Column chromatography on Silica Gel 60 (60–200 mesh) using 1:3 ethyl ether/chloroform as eluant gave 0.57 g as a colorless oil; IR (neat) 2935, 1735, 1670, 1615, 1450, 1410, 1370, 1215, 1145, 1110, 1045, 87, and 750 cm$^{-1}$; NMR (CDCl$_3$) $\delta$1.38 (t, J=7 Hz), 3.65 (d of d, 2H), 4.62 (qu., 2H, J=7 Hz) 5.85 (s, 1H).

h. 19-mercapto-androst-4-en-3,17-dione

Ethylenediamine (0.42 g, 0.47 ml, 7 mmol) was added under nitrogen to a stirred solution of 19-ethylxanthogen-4-androsten-3,17-dione (0.57 g, 1.40 mmol) in 10 ml dry THF. After 30 minutes at room temperature, 10 ml of a cold 1.0M H$_2$SO$_4$ solution was added and the reaction mixture was extracted twice with 25 ml ethyl ether. The organic phases were combined and washed three times with water, dried over MgSO$_4$, filtered, and concentrated on the rotary evaporator. The crude product (0.31 g) was recrystallized twice from methylcyclohexane to yield 160 mg of a white amorphous solid; mp 130°–133° C., $[\alpha]_D$ ($\alpha$=0.5 g/100 ml, chloroform)= +148°; UV (acetonitrile) $\lambda$max-235 nm; IR (neat) 2950, 2845, 2520, 1735, 1660, 1615, 1450, 1370, 1355, 1250, 1225; NMR (CDCl$_3$) 5.95 (s, 1H); MS m/z 318 (M+, 62), 285 (15), 272 (100), 271 (89), 253; Anal. C$_{19}$H$_{26}$O$_2$S C,H,O,S.

i. Biochemical Methods

Human placenta were obtained from the University Hospital, University of Washington, Seattle, WA, and were used within a few hours of delivery. Placental microsomes were prepared as previously described. (Coury et al). Protein concentration was determined by the method of Lowry (*J. Biol. Chem.*, 193, 265 (1951)).

j. Time-Dependent Inactivation Experiments

All incubations were carried out in 10 mM phosphate buffer, pH 7.5, 100 mM KCl, 1/mM EDTA. Incubations contained 1.0 mg/ml microsomal protein, 32 mg/ml propylene glycol, 0.36 mM NADPH, 11.5 mM glucose-6-phosphate dehydrogenase and 10 mM MgCl$_2$ and were allowed to warm to 30° C. for 5 minutes. Inhibitors were added as 10 $\mu$l/ml from 10 $\mu$M stock solutions in ethanol to give final inhibitor concentrations of 100 nM. At various times, from 0 to 70 minutes, 400 $\mu$l aliquots in duplicate were removed and were added to 100 ml of a 10 mM phosphate buffer, pH 7.5, 100 mM KCl, 1 mM EDTA containing 40 $\mu$M 1$\beta$,2$\beta$,[$^3$H]androstenedione (20 Ci/mol). Tritium release incubations were conducted at 37° C. for 10 minutes and stopped by addition of 5 ml 20% acetone/chloroform. Following vortexing at high speeds for 30 seconds and centrifugation, 100 $\mu$l of the water layer was removed and mixed with 5 ml LSC cocktail and counted. Percent activity remaining is the number of DPMs after a time period divided by the number of DPMs at time zero multiplied by 100.

k. Concentration-Dependent Inactivation Experiments

Incubations containing 1.0 mg/ml microsomal protein, 32 mg/ml propylene glycol, and 0.36 mM NADPH were warmed to 30° C. for 5 minutes. Various concentrations of inhibitor were added to the incubations in ethanol (10 $\mu$l/ml of incubate). Ethanol (10 $\mu$l/ml was) added as a control. After incubating 0, 1, 2, and 3 minutes at 30° C., 400 $\mu$l aliquots, in duplicate, were removed and were added to the tritium release assay described above.

l. NADPH Dependency Experiments

Incubations containing 1.0 mg/ml microsomal protein, 32 mg/ml propylene glycol, with or without 0.36 mM NADPH, were warmed to 30° C. for 5 minutes. Inhibitors were added in ethanol (10 $\mu$l/ml of incubate) to give inhibitor concentrations of 500 nM. Controls contained only ethanol and NADPH. After incubating 0 and 3 minutes at 30° C., 400 $\mu$l aliquots, in duplicate, from the NADPH containing incubations were added to the tritium release assay. For incubations lacking NADPH, 400 $\mu$l aliquots were removed and added to 100 $\mu$l phosphate buffer containing 1.4 mM NADPH and 40 $\mu$l 1$\beta$,2$\beta$[$^3$H]androstenedione (20 Ci/mol). Tritium release assays were conducted as described above.

m. Oxygen Dependency Experiments

Incubations containing 1.0 mg/ml microsomal protein, 32 mg/ml propylene glycol, and 500 nM inhibitor or ethanol (10 $\mu$l/ml) were prepared. Incubations run under anaerobic conditions were alternately evacuated and purged with deoxygenated nitrogen ten times at 0° C. Both anaerobic and aerobic incubations were allowed to warm to 30° C. for 5 minutes, and 10 $\mu$l/ml of a 1.4 mM NADPH solution was added via a syringe. After incubating 0 and 3 minutes at 30° C., triplicate aliquots of 400 $\mu$l were removed and added to tritium release assays.

n. Androstenedione Protection Experiments

Incubations containing 1.0 mg/ml microsomal protein, 32 mg/ml propylene glycol, and 0.36 mM NADPH were warmed to 30° C. for 5 minutes. Addition of ethanol solutions (10 μl/ml) of inhibitors with and without androstenedione gave final concentrations of 500 nM 17β-hydroxy-10β-mercaptoestr-4-en-3-one, 167 nM 19-mercaptoandrost-4-en-3,17-dione, with and without 5.0 μM androstenedione. After 0, 1, 2, and 3 minutes at 30° C., 400 μl aliquots, in duplicate, were removed and added to the tritium release assay.

o. Cysteine Protection Experiments

Incubations containing 1.0 mg/ml microsomal protein, 32 mg/ml propylene glycol, and 0.36 mM NADPH, with or without 1.0 mM cysteine, were warmed to 30° C. for 5 minutes. Addition of inhibitor solution (10 μl/ml) gave final concentrations of 500 nM 17β-hydroxy-10β-mercapto-4-en-3-one and 167 nM 19-mercaptoandrost-4-en-3,17-dione. After incubating 0, 1, 2, and 3 minutes, 400 μl aliquots, in duplicate, were removed and added to tritium release assays.

p. Irreversibility Experiments

Incubations containing 1.8 mg/ml microsomal protein, 32 mg/ml propylene glycol, 0.7 mM NADPH, and 250 nM of inhibitor were kept at 4° C. For zero time points, 400 μl aliquots, in triplicate, were removed and added to tritium release assays. Remaining microsomes were incubated at 30° C. for 5 minutes, cooled in ice to 4° C.; and 400 μl aliquots, in triplicate, were added to tritium release assays to determine remaining activity. Remaining microsomes were added to dialysis tubing (Spectrapore ® membrane tubing, 3500 dalton cut off) and dialyzed against a 10 mM phosphate buffer, pH 7.5, 100 mM KCl, 1 mM EDTA, and 5% propylene glycol at 0° C. for 20 hours. To serve as controls, incubations containing the same concentrations of inhibitor, but no cofactors, were carried through the same procedures.

After dialysis, 400 μl aliquots, in duplicate, were added to 100 μl phosphate buffer containing 2.9 mM NADPH and 40 μM 1β,2β[³H]androstenedione (20 Ci/mol) and incubated at 37° C. for 10 minutes. The usual workup for the tritium release assay was followed. Protein content for all incubations fell approximately 25% after dialysis. Enzyme activity fell approximately 60% after dialysis.

TABLE I

NADPH and Oxygen Dependency Experiments (500 nM).

| Inhibitor and Conditions | % Activity Remaining[a,b,c] (mean ± SD) |
|---|---|
| 1 | 67 ± 2 |
| 2 | 77 ± 4 |
| 1 − NADPH | 96 ± 3 |
| 2 − NADPH | 95 ± 5 |
| 1 + N₂ atmosphere | 95 ± 2 |
| 2 + N₂ atmosphere | 95 ± 5 |

[a]Preincubations with inhibitors were done for 3 minutes at 30° C.
[b]Values are not corrected for background loss of enzymatic activity since background losses under all three conditions were approximately 5%. Background loss is the amount of enzymatic activity lost with no inhibitor present.
[c]Assays were done in triplicate, N = 9.
1 = 17β-hydroxy-10β-mercaptoestr-4-en-3-one
2 = 19-mercaptoandrost-4-en-3,17-dione

TABLE II

Protection Studies of Either Androstenedione or Cysteine (1.0 mM) for Mercaptosteroids.

| Inhibitor and Conditions | $t_{\frac{1}{2}}$, sec.[a,b] (mean ± SD) |
|---|---|
| 1 | 281 ± 50 |
| 2 | 462 ± 75 |
| 1 and cysteine | 310 ± 58 |
| 2 and cysteine | 412 ± 20 |
| 1 and androstenedione | 756 ± 50 |
| 2 and androstenedione | 729 ± 21 |

[a]$T_{\frac{1}{2}}$ values represent the time it would take for 1 and 2 to bring about a 50% inhibition of aromatase.
[b]$T_{\frac{1}{2}}$ values are not corrected for background loss of enzymatic activity since background losses were the same under all three conditions.
1 = 17β-hydroxy-10β,-mercaptoestr-4-en-3-one
2 = 19-mercaptoandrost-4-en-3,17-dione

TABLE III

Irreversibility Experiments.

| | Activity Remaining[a,b] (mean ± SD) | |
|---|---|---|
| Inhibitor | Before Dialysis | After Dialysis |
| 1 | 49 ± 6% | 52 ± 3% |
| 2 | 50 ± 5% | 58 ± 2% |

[a]Preincubations with inhibitors were done for 5 minutes at 30° C.
[b]Assays were done in duplicate; therefore, mean and standard deviation values were calculated using N = 4.
1 = 17β-hydroxy-10β-mercaptoestr-4-en-3-one
2 = 19-mercaptoandrost-4-en-3,17-dione While preferred embodiments have been shown and described and several examples given, those skilled in the art will readily recognize variations and modifications which might be made without departing from the invention. The description is meant to illustrate the invention, not to limit it. The claims should be interpreted to protect the invention and should be limited only as necessary in view of the pertinent prior art.

We claim:

1. A method for inhibiting the enzymatic activity of aromatase for coverting $C_{19}$ androgens having a $\Delta^4$,3-ketone group to $C_{18}$ estrogens, comprising the step of:
    adding to a solution of aromatase an effective amount of a pharmaceutically active synthetic hormone selected from the group of compounds consisting of:

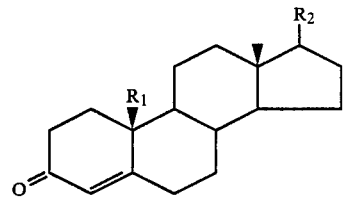

and mixtures thereof, wherein
$R_1 = -SH$ and
$R_2 = \blacktriangleleft OH$ or $=O$.

2. The method of claim 1 wherein the solution includes an effective amount of NADPH and oxygen.

3. The method of claim 1 wherein the hormone is selected from the group of compounds consisting of:

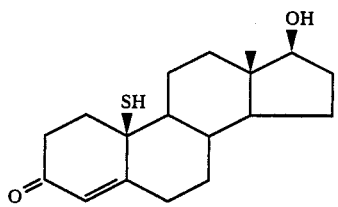

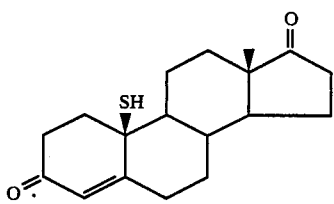

and mixtures thereof.

4. The method of claim 3 wherein the solution includes an effective amount of NADPH and oxygen.

5. The method of claim 1 wherein the hormone is:

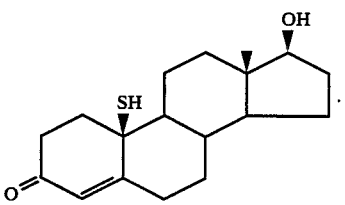

6. The method of claim 1 wherein the hormone is:

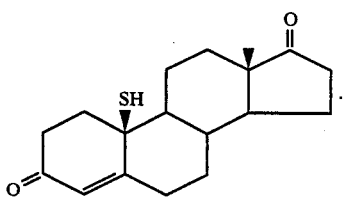

7. The method of claim 1 wherein the aromatase is human aromatase.

8. A method for treating estrogen-dependent breast tumors by inhibiting the formation of estrogen from $C_{19}$ androgens having a $\Delta^4$,3-ketone group, such an androstenedione, comprising the step of:

administering an effective amount of a pharmaceutically active, synthetic hormone to the patient, the hormone selected from the group consisting of:

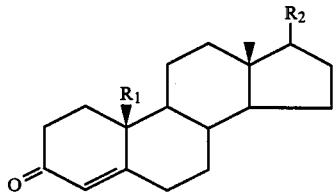

and mixtures thereof, wherein
$R_1 = $ —SH, and
$R_2 = $ ⟨OH or =O.

9. The method of claim 8 wherein the hormone is selected from the group consisting of:

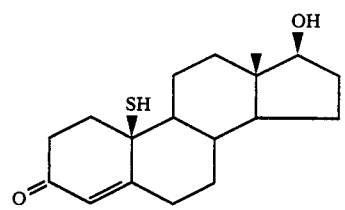

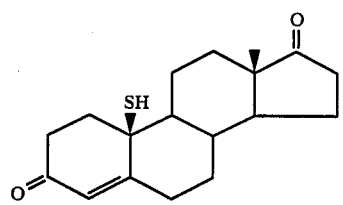

and mixtures thereof.

10. The method of claim 8 wherein the hormone is:

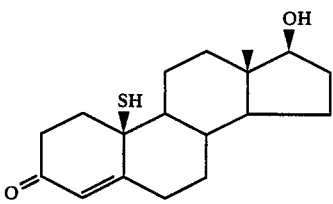

11. The method of claim 8 wherein the hormone is:

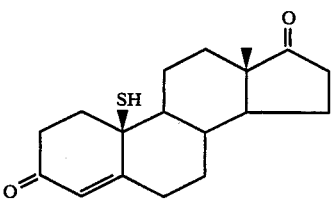

12. A suicide inhibitor for human aromatase in the presence of NADPH to inhibit the activity of aromatase for converting $C_{19}$ androgens having a $\Delta^4$,3-ketone group to $C_{18}$ estrogens, the inhibitor comprising:

a pharmaceutically active, synthetic hormone having a testosterone ring system backbone, a B-thiol substituent at the 10 carbon of the backbone, and a =O at the 17 carbon of the backbone, so that the hormone has the generalized structure:

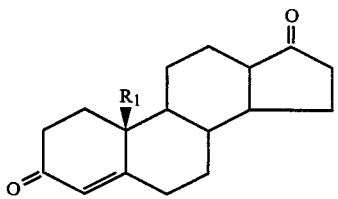

wherein $R_1 = $ the thiol substituent.

13. The inhibitor of claim 12 wherein the thiol substituent is —SH or —CH$_2$SH.

14. The inhibitor of claim 12 wherein the hormone is androst-4-en-3,17-dione.

15. The inhibitor of claim 12 wherein the hormone is:

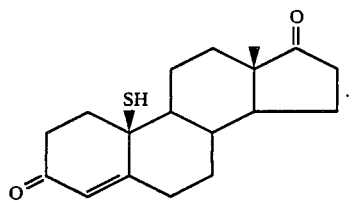

16. A method for making a thiol steroid from the corresponding alcohol without loss of unsaturation or carboxyl functionalities, comprising the steps of:

(a) activating the alcohol to a triflate by reacting the alcohol with trifluoromethanesulfonic anhydride;

(b) converting the triflate to a xanthogenate by reacting the triflate with potassium ethylxanthogenate in 18-crown-6 ether; and (c) cleaving the xanthogenate ether to the thiol by reacting the xanthogenate with ethyldiamine in tetrahydrofuran.

17. The method of claim 16 wherein the alcohol is:

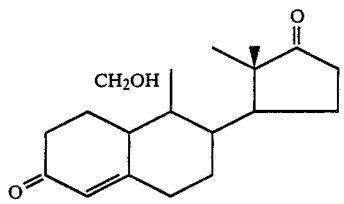

and the thiol product is:

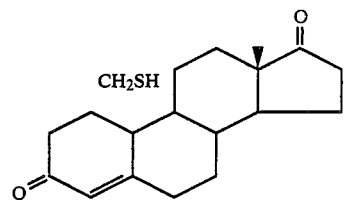

18. A method for making an unsaturated β-thiol steroid having a testosterone ring system backbone, comprising the steps of:

(a) creating a β-halohydrin by reacting N-halosuccinimide with an unsaturated testosterone ring system steroid;

(b) reacting the β-halohydrin with a base to form an α-epoxide bridging the carbons which were originally unsaturated;

(c) reacting the epoxide with an alkali hydrogen sulfide to form a hydroxymercapto steroid; and (d) dehydrating the hydroxymercapto steroid to form the β-thiol, unsaturated steroid.

* * * * *